United States Patent
Chung et al.

(10) Patent No.: US 10,113,980 B2
(45) Date of Patent: Oct. 30, 2018

(54) FURNACE FOR TRANSMISSION MODE X-RAY DIFFRACTOMETER AND TRANSMISSION MODE X-RAY DIFFRACTOMETER USING THEREOF

(71) Applicant: KOREA INSTITUTE OF SCIENCE AND TECHNOLOGY, Seoul (KR)

(72) Inventors: Kyung Yoon Chung, Seoul (KR); Dong Hyun Kim, Seoul (KR); Susanto Dieky, Seoul (KR); Yeojo Yoon, Seoul (KR); Byung Won Cho, Seoul (KR); Si Hyoung Oh, Seoul (KR); Won Young Chang, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 154 days.

(21) Appl. No.: 15/099,678

(22) Filed: Apr. 15, 2016

(65) Prior Publication Data
US 2017/0212062 A1 Jul. 27, 2017

(30) Foreign Application Priority Data

Jan. 22, 2016 (KR) .......... 10-2016-0007916

(51) Int. Cl.
*H05G 1/34* (2006.01)
*G01N 1/44* (2006.01)
(Continued)

(52) U.S. Cl.
CPC ......... *G01N 23/20025* (2013.01); *G01N 1/44* (2013.01); *G01N 23/20008* (2013.01);
(Continued)

(58) Field of Classification Search
CPC .. H05G 1/00; H05G 1/02; H05G 1/04; H05G 1/08; H05G 1/26; H05G 1/30; H05G 1/34; G01N 23/00; G01N 23/20; G01N 23/20008; G01N 23/20025; G01N 23/20033; G01N 23/207; G01N 2223/00; G01N 2223/05; G01N 2223/056; G01N 2223/0566; G01N 2223/20; G01N 2223/30; G01N 2223/307;
(Continued)

(56) References Cited

U.S. PATENT DOCUMENTS 6,528,018 B1 * 3/2003 Berndt ................. G01N 21/714
422/550
8,256,232 B2 * 9/2012 Burg ........................ A01N 1/02
62/66
(Continued)

FOREIGN PATENT DOCUMENTS

JP          8-128972 A      5/1996
JP       2000-40483 A      2/2000
KR    1020120124102 B1    11/2012

*Primary Examiner* — Anastasia Midkiff
(74) *Attorney, Agent, or Firm* — Goldilocks Zone IP Law

(57) ABSTRACT

Provided is a furnace for a transmission mode X-ray diffractometer and a transmission mode X-ray diffractometer using the same. The furnace for a transmission mode X-ray diffractometer includes a sample heating unit disposed adjacent to a quartz capillary accommodating a sample to heat the sample, and a main body disposed to surround the quartz capillary and the sample heating unit and having an insulating function for allowing the heated sample to maintain a thermal equilibrium state.

12 Claims, 2 Drawing Sheets

(51) Int. Cl.
*G01N 23/20* (2018.01)
*G01N 23/20025* (2018.01)
*G01N 23/20033* (2018.01)
*G01N 23/20008* (2018.01)
*G01N 23/207* (2018.01)

(52) U.S. Cl.
CPC ......... G01N 23/20033 (2013.01); H05G 1/34 (2013.01); *G01N 23/207* (2013.01); *G01N 2223/309* (2013.01); *G01N 2223/3106* (2013.01)

(58) Field of Classification Search
CPC ......... G01N 2223/309; G01N 2223/31; G01N 2223/3106; G01N 2223/32; G01N 2223/40; G01N 2223/60; G01N 2223/605; G01N 1/00; G01N 1/44
See application file for complete search history.

(56) References Cited

U.S. PATENT DOCUMENTS

| | | | | |
|---|---|---|---|---|
| 2005/0069084 A1* | 3/2005 | Blomsma | ............... | G01N 23/20 378/70 |
| 2009/0213992 A1* | 8/2009 | Iwasaki | ............... | G01N 23/201 378/86 |
| 2013/0052100 A1* | 2/2013 | Claeys | ............. | G01N 23/20033 422/546 |
| 2014/0377880 A1* | 12/2014 | Emburgh | ................. | B01L 3/04 436/175 |

\* cited by examiner

FURNACE FOR TRANSMISSION MODE X-RAY DIFFRACTOMETER AND TRANSMISSION MODE X-RAY DIFFRACTOMETER USING THEREOF

CROSS-REFERENCE TO RELATED APPLICATIONS

This application claims priority under 35 U.S.C. § 119 to Korean Patent Application No. 10-2016-0007916 filed on Jan. 22, 2016 in the Korean Intellectual Property Office, the disclosure of which is incorporated herein by reference in its entirety.

TECHNICAL FIELD

The following disclosure relates to a furnace for a transmission mode X-ray diffractometer and a transmission mode X-ray diffractometer using the same, and in particular, to a furnace for a transmission mode X-ray diffractometer and a transmission mode X-ray diffractometer using the same, which may allow a phase change of a sample according to a temperature change to be observed in real time.

BACKGROUND

X-ray diffractometry (XRD) using X-ray diffraction is frequently used for the purpose of phase analysis or the like of various materials such as liquid, metal, inorganic substances, polymers, catalysts, plastic, prepared medicines, thin film coating, ceramics and semiconductors.

The X-ray diffractometry becomes one of essential methods for raw material investigation, characterization, quality management in industries and research agencies, and is actually applied to broad fields such as investigation of process automation or large amount of polymorph as well as investigation of quantitative analysis, qualitative analysis, crystallography, structure and relaxed condition, tissue and residual stress, controlled sample environments, micro diffraction, nano substances or the like.

In particular, the X-ray diffractometry represents analysis of a crystal structure among molecules, and a device for X-ray diffractometry demands high accuracy, high precision and high reliability.

In addition, the X-ray diffractometry is classified into a reflection mode and a transmission mode, and when observing a phase change of a sample according to a temperature change, the reflection mode X-ray diffractometry takes 20 to 30 minutes for analyzing diffraction of the sample at a specific temperature and thus is not suitable for measuring a phase change of a sample according to a temperature change in real time.

In other words, the reflection-type X-ray diffractometry takes 20 to 30 minutes for performing diffractometry to a sample at a specific temperature, and thus when it is intended to observe a phase change of a sample, generated for several minutes (for example, 1 to 5 minutes), or it is intended to observe a sample accompanied with various phase changes during several minutes, there is a limit in observing detailed phase changes of the corresponding sample. This limit of the reflection-type X-ray diffractometry may be solved by means of the transmission-type X-ray diffractometry which takes just several minutes for measuring data of each sample.

In addition, in existing transmission mode X-ray diffractometry, when measuring a phase change of a sample according to a temperature change, the phase change of the sample may not be stably measured at a high temperature range of 400 to 500° C. Moreover, since a temperature deviation at the high temperature range is up to ±40° C., a thermal equilibrium state may not be easily maintained, and thus it is not easy to obtain reliable data.

Thus, when observing a phase change of a sample according to a temperature change, it is demanded to develop a device capable of heating a sample to a high temperature and easily maintaining a thermal equilibrium state of the sample at the high temperature, when observing a phase change of the sample according to a temperature change.

RELATED LITERATURES

Patent Literature

Korean Patent Registration No. 10-1274290 (published on Jun. 13, 2013)

SUMMARY

An embodiment of the present disclosure is directed to providing a furnace for a transmission mode X-ray diffractometer and a transmission mode X-ray diffractometer using the same, which may allow a phase change of a sample according to a temperature change to be stably observed in real time.

In one general aspect, the present disclosure provides a furnace for a transmission mode X-ray diffractometer, comprising: a sample heating unit disposed adjacent to a quartz capillary accommodating a sample to heat the sample; and a main body disposed to surround the quartz capillary and the sample heating unit and having an insulating function for allowing the heated sample to maintain a thermal equilibrium state.

The main body may include: a first through hole into which an X-ray is input; and a second through hole provided to face the first through hole with the quartz capillary being interposed therebetween, so that the X-ray passing through the sample and diffracted by the sample is emitted from the second through hole.

The second through hole may be tapered according to a diffraction angle of the X-ray to have a diameter gradually increasing from an inlet at which the X-ray is input toward an outlet at which the X-ray is diffracted and emitted, so that the X-ray passing through the sample is not interfered.

The sample heating unit may include a heating coil disposed adjacent to the quartz capillary to surround the quartz capillary.

The sample heating unit may further include an insulating member disposed to surround the heating coil and having an insulating function so that the sample heated by the heating coil maintains a thermal equilibrium state.

The insulating member may be configured with a quartz tube disposed to surround the heating coil.

The quartz tube may include: a third through hole configured to communicate with the first through hole, so that the X-ray passing through the first through hole is input thereto, the third through hole having a diameter corresponding to the first through hole; and a fourth through hole provided to communicate with the third through hole and to face the third through hole with the quartz capillary being interposed therebetween, the fourth through hole communicating with the second through hole so that the X-ray passing through the sample and diffracted by the sample is emitted to the second through hole, wherein the fourth through hole may be tapered to have a diameter gradually increasing according to a diffraction angle of the X-ray from an inlet at which the X-ray passing through the sample is input toward an outlet at which the X-ray is diffracted and emitted, so that the X-ray passing through the sample is not interfered.

The first to fourth through holes may be arranged in line, and an inclination angle of the fourth through hole may be identical to an inclination angle of the second through hole.

The main body may further include a mounting groove provided therein so that the quartz tube is mounted therein.

In another aspect of the present disclosure, there is provided a transmission mode X-ray diffractometer, comprising: an X-ray generation unit configured to generate an X-ray; a furnace configured to receive a quartz capillary accommodating a sample to which the X-ray is irradiated and to heat the sample and allow the heated sample to maintain a thermal equilibrium state in order to observe a phase change of the sample, which occurs during a temperature rise; and an X-ray detection unit disposed to face the X-ray generation unit with the furnace being interposed therebetween, the X-ray detection unit detecting the X-ray which passes through the sample and is diffracted by the sample.

The transmission mode X-ray diffractometer may further comprise a temperature sensor inserted into the furnace to measure a heating temperature of the furnace.

In the embodiment of the present disclosure, by heating a sample to a high temperature and maintaining a thermal equilibrium state of the heated sample, a phase change of the sample according to a temperature rise may be easily observed in real time.

DETAILED DESCRIPTION OF EMBODIMENTS

Figure 1:
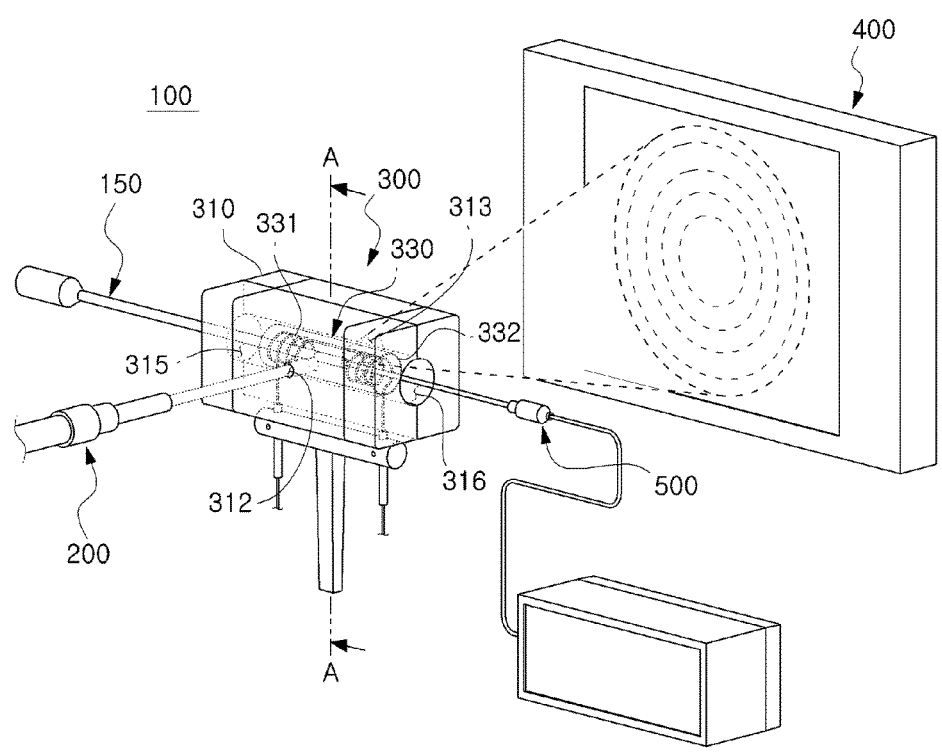
FIG. 1 is a diagram schematically showing a transmission mode X-ray diffractometer according to an embodiment of the present disclosure.

The present disclosure, advantages of operations of the present disclosure and objects accomplished by the implementation of the present disclosure can be sufficiently understood with reference to the accompanying drawings depicting embodiments of the present disclosure and explanations thereof.

Hereinafter, an embodiment of the present disclosure will be described in detail with reference to the accompanying drawings. In the drawings, like reference numerals denote like elements.

Figure 2:
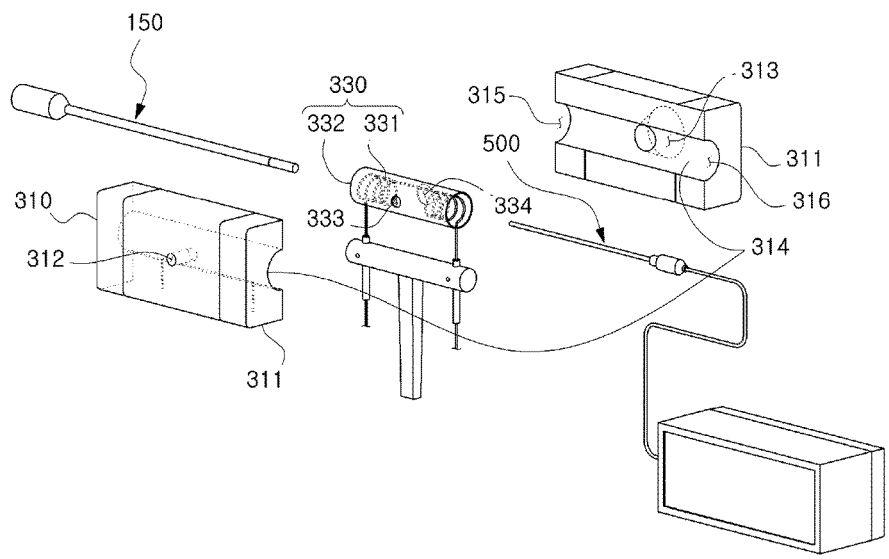
FIG. 2 is an exploded perspective view showing a furnace according to an embodiment of the present disclosure.
Figure 3:
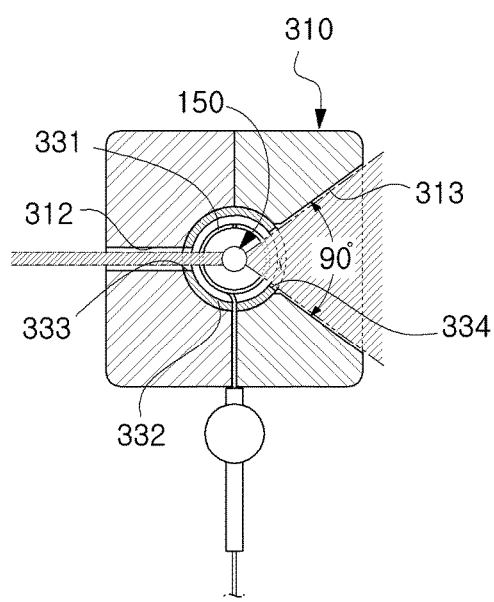
FIG. 3 is a cross-sectional view showing the furnace according to an embodiment of the present disclosure, taken along the line A-A of FIG. 1.

FIG. 1 is a diagram schematically showing a transmission mode X-ray diffractometer according to an embodiment of the present disclosure, FIG. 2 is an exploded perspective view showing a furnace according to an embodiment of the present disclosure, and FIG. 3 is a cross-sectional view showing the furnace according to an embodiment of the present disclosure, taken along the line A-A of FIG. 1.

Referring to FIG. 1, a transmission mode X-ray diffractometer 100 according to an embodiment of the present disclosure includes an X-ray generation unit 200 configured to generate an X-ray, a furnace 300 configured to accommodate a sample to which the X-ray is irradiated and to heat the sample and allow the heated sample to maintain a thermal equilibrium state in order to observe a phase change of the sample, which occurs during a temperature rise, and an X-ray detection unit 400 disposed to face the X-ray generation unit 200 with the furnace 300 being interposed therebetween and to detect the X-ray which passes through the sample and is diffracted by the sample.

The transmission mode X-ray diffractometer 100 according to an embodiment of the present disclosure irradiates the X-ray generated by the X-ray generation unit 200 to the sample in the furnace 300 and detects the X-ray passing through the sample and diffracted by the sample by means of the X-ray detection unit 400.

In addition, the transmission mode X-ray diffractometer 100 according to an embodiment of the present disclosure may heat the sample in the furnace 300 and observe a phase change of the sample during a temperature rise in real time.

Moreover, in the transmission mode X-ray diffractometer 100 according to an embodiment of the present disclosure, by stably maintaining the thermal equilibrium state of the sample, it is possible to prevent any error from being generated due to a temperature deviation, when observing a phase change of the sample during a temperature rise.

In addition, in the transmission mode X-ray diffractometer 100 according to an embodiment of the present disclosure, the furnace 300 is configured to accommodate the sample and to heat the same. Also the furnace 300 maintains a thermal equilibrium state of the heated sample.

The X-ray generation unit 200 according to this embodiment plays a role of focusing X-rays irradiated to the sample and irradiating X-rays to the sample in a linear form as a parallel ray, a non-divergent beam.

If X-rays are irradiated to the sample, a diffraction phenomenon occurs only in a specific direction. Here, since diffraction peaks generated by such diffraction phenomenon have inherent lattice constant and atomic layer structure for each substance and thus a diffraction peak can be observed only at a specific location for each substance, a phase of the material may be analyzed by means of the diffraction peak.

In this embodiment, the X-ray irradiated to the sample passes through the sample and is diffracted by the sample, and is then detected by the X-ray detection unit 400 disposed to face the X-ray generation unit 200.

In this embodiment, a furnace 300 is provided to accommodate the sample so that a phase change of the sample according to a temperature change may be observed in real time.

The furnace 300 according to this embodiment accommodates the sample and plays a role of heating the sample and allowing the heated sample to maintain a thermal equilibrium state.

In detail, referring to FIGS. 2 and 3, the furnace 300 according to this embodiment includes a sample heating unit 330 disposed adjacent to the quartz capillary 150 accommodating the sample to heat the sample, and a main body 310 disposed to surround the quartz capillary 150 and the sample heating unit 330 and having an insulating function so that the heated sample may maintain a thermal equilibrium state.

The main body 310 gives an insulating function for stably maintaining a thermal equilibrium state of the sample heated by the sample heating unit 330, explained later, to prevent an error from being generated due to a temperature deviation, and preventing a heat loss when heating the sample to a high temperature.

Even though it is depicted that the main body 310 is formed by coupling a pair of unit blocks 311 to each other, the present disclosure is not limited thereto, and the main body may be formed with an integral block.

In addition, the quartz capillary 150 accommodating the sample is inserted into the main body 310, and a capillary insert hole 315 may be formed at one side of the main body 310 so that the quartz capillary 150 is inserted therein. A sample to be observed is accommodated in the quartz capillary 150, and the quartz capillary 150 is inserted into and mounted to the main body 310 through the capillary insert hole 315 formed at one side of the main body 310.

In addition, the main body 310 further includes a first through hole 312 to which an X-ray is input from the X-ray generation unit 200, and a second through hole 313 provided to communicate with the first through hole 312 and to face the first through hole 312 with the quartz capillary 150 being interposed therebetween so that the X-ray passing through the sample and diffracted by the sample is emitted therefrom.

The first through hole 312 and the second through hole 313 are arranged in line with an advancing direction of the X-ray to communicate with each other. Therefore, the X-ray is input to the first through hole 312, passes through the sample and is diffracted by the sample, and then is emitted toward the X-ray detection unit 400 via the second through hole 313.

In addition, since the X-ray input from the X-ray generation unit 200 is a parallel ray with a linear form, the first through hole 312 is formed with a hole shape parallel to the X-ray so that the X-ray may pass therethrough.

In addition, the second through hole 313 is formed with a shape corresponding to a diffraction angle of the X-ray since the X-ray passing through the sample and diffracted by the sample is input and emitted.

In detail, as shown in FIG. 3, the second through hole 313 is tapered to have a diameter gradually increasing according to the diffraction angle of the X-ray so that the X-ray passing through the sample is not interfered by the main body 310.

In other words, the second through hole 313 has a diameter gradually increasing from an inlet at which an X-ray passing through the sample is input to an outlet at which the X-ray is emitted toward the X-ray detection unit 400.

In this embodiment, since the X-ray diffracted by the sample has a conical shape, the second through hole 313 may have a conical shape tapered in a lengthwise direction correspondingly. However, the present disclosure is not limited thereto, and the second through hole 313 may also have a shape tapered in a lengthwise direction with a polygonal section as long as the X-ray of a conical shape is not interfered. In addition, even though FIG. 3 depicts that the second through hole 313 has a conical shape with an angle of 90°, this may be modified according to the diffraction angle of the X-ray.

Meanwhile, the transmission mode X-ray diffractometer 100 according to the present disclosure heats a sample inserted into the main body 310, allows a phase change occurring at the sample which is being heated to be observed in real time, and stably maintains a thermal equilibrium state of the sample while the phase change of the sample is being observed, to prevent an error from being generated due to a temperature deviation.

For this, the furnace 300 according to this embodiment includes a sample heating unit 330 provided in the main body 310 and disposed adjacent to the quartz capillary 150 inserted into the main body 310 to heat a sample and maintain a thermal equilibrium state of the heated sample.

The sample heating unit 330 includes a heating coil 331 disposed adjacent to the quartz capillary 150 and configured to surround the quartz capillary 150, and an insulating member 332 disposed to surround the heating coil 331 and having an insulating function to maintain a thermal equilibrium state of the sample heated by the heating coil 331.

In addition, in this embodiment, the insulating member 332 may be configured with a quartz tube 332 disposed to surround the heating coil 331.

The quartz tube 332 according to this embodiment is placed and mounted in the main body 310. For this, the main body 310 further includes a mounting groove 314 provided therein so that the quartz tube 332 is mounted therein.

As shown in FIGS. 2 and 3, if the main body 310 is formed with a pair of unit blocks 311, the main body 310 has a mounting groove 314 at a surface where the pair of unit blocks 311 is coupled to each other.

The quartz tube 332 is mounted or inserted into the mounting groove 314 provided at the pair of unit blocks 311, and then the pair of unit blocks 311 is coupled to each other to mount the quartz tube 332 to the main body 310.

Meanwhile, before the quartz tube 332 is mounted to the main body 310, the heating coil 331 is installed at an inner surface of the quartz tube 332.

The heating coil 331 is disposed at the inner surface of the quartz tube 332 to surround the quartz capillary 150 inserted into the main body 310 and the quartz tube 332. Though not shown in the figures, the heating coil 331 is connected to a coil control unit (not shown), and the coil control unit controls a heating temperature of the heating coil 331.

As described above, in this embodiment, the sample is heated by the heating coil 331 disposed to surround the quartz capillary 150, and the quartz tube 332 has an insulating function for maintaining the heated sample at a certain temperature (a thermal equilibrium state of the sample).

As described above, by using the furnace 300 of this embodiment including the main body and the quartz tube having an insulating function and the heating coil 331, the sample may be heated to a high temperature region of 1000° C. or above, and a thermal equilibrium state of the heated sample may be maintained. In detail, if the furnace 300 of this embodiment is used, a thermal equilibrium state of the sample may be stably maintained with a temperature deviation of ±0.5° C., even at a high temperature region of 1000° C. or above.

Therefore, in order to find out a temperature at which a structure of a compound is formed in the field of ceramic where powder is generally synthesized in a high temperature range of about 800° C., the furnace 300 of this embodiment may find a temperature at which a specific structure is formed, just once in real time while heating the sample, without separately performing a synthesizing process at temperatures of 700° C., 750° C., 800° C. or the like.

In addition, the transmission mode X-ray diffractometer 100 according to the present disclosure further includes a temperature sensor 500 inserted into the furnace 300, in more detail into the quartz tube 332, to measure a heating temperature of the heating coil 331.

In addition, a sensor insert hole 316 may be formed at the other side of the main body 310 so that the temperature sensor 500 may be inserted therein. The temperature sensor 500 is inserted into the main body 310 and the quartz tube 332 through the sensor insert hole 316 formed at the other side of the main body 310.

The transmission mode X-ray diffractometry requires about 1 minute for observing a diffraction phenomenon of the sample, and thus the transmission mode X-ray diffractometer 100 according to an embodiment of the present disclosure heats the sample by using the heating coil 331, measures a temperature of the sample by using the temperature sensor 500, and maintains the temperature of the sample consistently by means of the insulating function of the main body 310 and the quartz tube 332 while a phase change of the sample is being observed.

Therefore, the transmission mode X-ray diffractometer 100 according to an embodiment of the present disclosure may maintain the temperature of the sample consistently while observing a phase change of the sample according to a temperature change, and thus a phase change of the sample according to a temperature change may be stably observed.

Meanwhile, since the quartz tube 332 is located on an advancing path of the X-ray, the quartz tube 332 has a third through hole 333 and a fourth through hole 334 arranged in line with the first through hole 312 and the second through hole 313 on an advancing path of the X-ray so as not to interfere or disturb the advancing path of the X-ray.

In detail, as shown in FIG. 3, the quartz tube 332 includes a third through hole 333 configured to communicate with the first through hole 312, so that the X-ray passing through the first through hole 312 is input thereto, and having a diameter corresponding to the first through hole 312, and a fourth through hole 334 provided to communicate with the third through hole 333 and to face the third through hole 333 with the quartz capillary 150 being interposed therebetween, the fourth through hole 334 communicating with the second through hole 313 so that the X-ray passing through the sample and diffracted by the sample is emitted to the second through hole 313.

Since the X-ray input through the first through hole 312 is a parallel ray with a linear shape, the third through hole 333 is formed with a hole shape parallel to the X-ray so that the X-ray may pass through the third through hole 333.

In addition, since the X-ray passing through the sample and diffracted by the sample is input or emitted at the fourth through hole 334, the fourth through hole 334 has a shape corresponding to a diffraction angle of the X-ray.

In detail, as shown in FIG. 3, the fourth through hole 334 is tapered to have a diameter gradually increasing according to a diffraction angle of the X-ray, so that the X-ray passing through the sample is not interfered or disturbed by the quartz tube 332.

In other words, the fourth through hole 334 has is a diameter gradually increasing from an inlet at which the X-ray passing through the sample is input toward an outlet at which the X-ray is diffracted by the X-ray and emitted toward the second through hole 313 and the X-ray detection unit 400.

In addition, in this embodiment, since the X-ray diffracted by the sample has a conical shape, the fourth through hole 334 may have a conical shape tapered in a lengthwise direction correspondingly. However, the present disclosure is not limited thereto, and the fourth through hole 334 may also have a shape tapered in a lengthwise direction with a polygonal section as long as the X-ray of a conical shape is not interfered.

In addition, an inclination angle of the fourth through hole 334 may be identical to an inclination angle of the second through hole 313, and the fourth through hole 334 and the second through hole 313 may have the same conical shape, so that the fourth through hole 334 and the second through hole 313 may be formed successively.

As described above, the X-ray irradiated from the X-ray generation unit 200 to the sample passes through the first through hole 312 and the third through hole 333 in order and is then diffracted by the sample, and the diffracted X-ray passes through the fourth through hole 334 and the second through hole 313 and is then irradiated to the X-ray detection unit 400. Therefore, the first to fourth through holes 312, 313,333,334 are arranged in line with each other along the advancing path of the X-ray.

Operations of the transmission mode X-ray diffractometer 100 according to an embodiment of the present disclosure, configured as above, will be described as follows.

As shown in FIG. 1, the sample heating unit 330 having the quartz tube 332 and the heating coil 331 provided at the inner surface of the quartz tube 332 is placed and mounted in the mounting groove 314 of the main body 310.

In addition, the quartz capillary 150 accommodating a sample is disposed at and inserted in the inside of the quartz tube 332 and the heating coil 331 through the capillary insert hole 315.

The sample is heated by the heating coil 331 surrounding the quartz capillary 150, and a heating temperature of the sample is measured by the temperature sensor 500. In addition, when a diffraction phenomenon is to be observed in a state where the sample is heated to a specific temperature, the heating temperature of the sample may be maintained consistently by means of the heating coil 331 as well as the main body 310 and the quartz tube 332 having an insulating function.

In addition, the X-ray generated by the X-ray generation unit 200 is irradiated to the sample along the first through hole 312 of the main body 310 and the third through hole 333 of the quartz tube 332.

The X-ray irradiated to the sample is diffracted by the sample and is then emitted to the X-ray detection unit 400 along the fourth through hole 334 of the quartz tube 332 and the second through hole 313 of the main body 310.

At this time, the fourth through hole 334 and the second through hole 313 are tapered to have a diameter gradually increasing along a lengthwise direction with an angle corresponding to the diffraction angle of the X-ray, so that the advancing path of the diffracted X-ray is not interfered or disturbed by the fourth through hole 334 and the second through hole 313.

The present disclosure is not limited to the embodiments described above, but it is obvious to those having ordinary skill in the art that the present disclosure may be changed or modified in various ways without departing from the scope thereof. Therefore, such changes or modifications should be regarded as falling into the scope of the appended claims.

REFERENCE SYMBOLS

| | |
|---|---|
| 100: X-ray diffractometer | 150: quartz capillary |
| 200: X-ray generation unit | 300: furnace |
| 310: main body | 311: unit block |
| 312: first through hole | 313: second through hole |
| 314: mounting groove | 315: capillary insert hole |
| 316: sensor insert hole | 330: sample heating unit |
| 331: heating coil | 332: quartz tube |
| 333: third through hole | 334: fourth through hole |
| 400: X-ray detection unit | 500: temperature sensor |

What is claimed is:

1. A furnace for a transmission mode X-ray diffractometer, comprising:
a sample heating unit disposed adjacent to a quartz capillary accommodating a sample to heat the sample; and a main body disposed to surround the quartz capillary and the sample heating unit and having an insulating function for allowing the heated sample to maintain a thermal equilibrium state, wherein the main body includes:

a first through hole into which an X-ray is input; and a second through hole provided to face the first through hole with the quartz capillary being interposed therebetween, so that the X-ray passing through the sample and diffracted by the sample is emitted from the second through hole, wherein the second through hole is tapered according to a diffraction angle of the X-ray to have a diameter gradually increasing from an inlet at which the X-ray is input toward an outlet at which the X-ray is diffracted and emitted, so that the second through hole does not interfere with the X-ray passing through the sample.

2. The furnace for a transmission mode X-ray diffractometer according to claim 1, wherein the sample heating unit includes a heating coil disposed adjacent to the quartz capillary to surround the quartz capillary.

3. The furnace for a transmission mode X-ray diffractometer according to claim 2, wherein the sample heating unit further includes an insulating member disposed to surround the heating coil and having an insulating function so that the sample heated by the heating coil maintains a thermal equilibrium state.

4. The furnace for a transmission mode X-ray diffractometer according to claim 3, wherein the insulating member is configured as a quartz tube disposed to surround the heating coil.

5. A furnace for a transmission mode X-ray diffractometer, comprising:

a sample heating unit disposed adjacent to a quartz capillary accommodating a sample to heat the sample, wherein the sample heating unit includes a heating coil disposed adjacent to the quartz capillary to surround the quartz capillary and an insulating member disposed to surround the heating coil and having an insulating function so that the sample heated by the heating coil maintains a thermal equilibrium state; and a main body disposed to surround the quartz capillary and the sample heating unit and having an insulating function for allowing the heated sample to maintain a thermal equilibrium state, wherein the insulating member is configured as a quartz tube disposed to surround the heating coil, wherein the main body includes:

a first through hole into which an X-ray is input, and a second through hole provided to face the first through hole with the quartz capillary being interposed therebetween, so that the X-ray passing through the sample and diffracted by the sample is emitted from the second through hole, wherein the quartz tube includes:

a third through hole configured to communicate with the first through hole, so that the X-ray passing through the first through hole is input thereto, the third through hole having a diameter corresponding to the first through hole, and a fourth through hole provided to communicate with the third through hole and to face the third through hole with the quartz capillary being interposed therebetween, the fourth through hole communicating with the second through hole so that the X-ray passing through the sample and diffracted by the sample is emitted to the second through hole, wherein the fourth through hole is tapered to have a diameter gradually increasing according to a diffraction angle of the X-ray from an inlet at which the X-ray passing through the sample is input toward an outlet at which the X-ray is diffracted and emitted, so that the fourth through hole does not interfere with the path of the X-ray passing through the sample.

6. The furnace for a transmission mode X-ray diffractometer according to claim 5, wherein the first to fourth through holes are arranged in line, and wherein an inclination angle of the fourth through hole is identical to an inclination angle of the second through hole.

7. The furnace for a transmission mode X-ray diffractometer according to claim 4, wherein the main body further includes a mounting groove such that the quartz tube is mounted within said mounting groove.

8. A transmission mode X-ray diffractometer, comprising:

an X-ray generation unit configured to generate an X-ray;

a furnace, as defined in claim 1, configured to receive the quartz capillary accommodating the sample to which the X-ray is irradiated and to heat the sample and allow the heated sample to maintain a thermal equilibrium state in order to observe a phase change of the sample, which occurs during a temperature rise; and an X-ray detection unit disposed to face the X-ray generation unit with the furnace being interposed therebetween, the X-ray detection unit detecting the X-ray which passes through the sample and is diffracted by the sample.

9. The transmission mode X-ray diffractometer according to claim 8, further comprising:

a temperature sensor inserted into the furnace to measure a heating temperature of the furnace.

10. The furnace for a transmission mode X-ray diffractometer according to claim 5, wherein the main body further includes a mounting groove such that the quartz tube is mounted within said mounting groove.

11. A transmission mode X-ray diffractometer, comprising:

an X-ray generation unit configured to generate an X-ray;

a furnace, as defined in claim 5, configured to receive the quartz capillary accommodating the sample to which the X-ray is irradiated and to heat the sample and allow the heated sample to maintain a thermal equilibrium state in order to observe a phase change of the sample, which occurs during a temperature rise; and an X-ray detection unit disposed to face the X-ray generation unit with the furnace being interposed therebetween, the X-ray detection unit detecting the X-ray which passes through the sample and is diffracted by the sample.

12. The transmission mode X-ray diffractometer according to claim 11, further comprising a temperature sensor inserted into the furnace to measure a heating temperature of the furnace.

* * * * *